United States Patent [19]
Flotte et al.

[11] Patent Number: 5,658,776
[45] Date of Patent: Aug. 19, 1997

[54] GENERATION OF HIGH TITERS OF RECOMBINANT AAV VECTORS

[75] Inventors: Terence R. Flotte, Glen Burnie, Md.; Barrie J. Carter, Seattle, Wash.; William B. Guggino, Baltimore; Rikki Solow, Gaithersburg, both of Md.

[73] Assignees: Targeted Genetics Corporation, Seattle, Wash.; Johns Hopkins University, Baltimore, Md.

[21] Appl. No.: 448,613

[22] Filed: Jun. 7, 1995

Related U.S. Application Data

[63] Continuation of PCT/US94/12587, Nov. 3, 1994, which is a continuation-in-part of Ser. No. 149,332, Nov. 9, 1993, abandoned.

[51] Int. Cl.$^6$ .............................. C12N 5/16; C12N 15/64; C12N 15/86
[52] U.S. Cl. .................... 435/172.3; 435/320.1; 435/91.4; 435/352; 435/363; 435/366; 435/367; 435/369; 435/371
[58] Field of Search ................... 435/69.1, 172.3, 435/240.2, 320.1, 91.33, 91.4, 91.41, 91.42

[56] References Cited

U.S. PATENT DOCUMENTS

| | | | |
|---|---|---|---|
| 4,797,368 | 1/1989 | Carter et al. | 435/320.1 |
| 5,139,941 | 8/1992 | Muzyczka et al. | 435/172.3 |
| 5,173,414 | 12/1992 | Lebkowski et al. | 435/172.3 |

FOREIGN PATENT DOCUMENTS

WO 91/18088  11/1991  WIPO.

OTHER PUBLICATIONS

Carter, B.J., "Adeno–associated virus vectors" *Current Opinion in Biotechnol.* (1992) 3:533–539.

Muzyczka, N., "Use of adeno–associated virus as a general transduction vector for mammalian cells" *Current Topics in Microbiology and Immunology* (1992) 158:97–129.

Flotte, T.R., et al., "Gene expression from adeno–associated virus vectors in airway epithelial cells" *Am. J. Respir. Cell Mol. Biol.* (1992) 7:349–356.

Egan, M., et al., "Defective regulation of outwardly rectifying Cl$^-$ channels by protein kinase A corrected by insertion of CFTR" *Nature* (1992) 358:581–584.

Flotte, T.R., et al., "Expression of the cystic fibrosis transmembrane conductance regulator from a novel adeno–associated virus promoter" *J. Biol. Chem.* (1993) 268:3781–3790. An author proof copy was previously enclosed.

Flotte, T.R., et al., "Stable in vivo expression of the cystic fibrosis transmembrane conductance regulator with an adeno–associated virus vector" *Proc. Natl. Acad. Sci. USA* (1993) 90:10613–10617.

Walsh, C.E., et al., "Regulated high level expression of human γ–globin gene introduced into erythroid cells by an adeno–associated virus vector" *Proc. Natl. Acad. Sci. USA* (1992) 89:7257–7261.

(List continued on next page.)

*Primary Examiner*—David Guzo
*Attorney, Agent, or Firm*—Morrison & Foerster L.P.P.

[57] ABSTRACT

Adeno-associated virus (AAV) vectors may have utility for gene therapy but heretofore a significant obstacle has been the inability to generate sufficient quantifies of such recombinant vectors in amounts that would be clinically useful for human gene therapy application. Stable, helper-free AAV packaging cell lines have been elusive, mainly due to the activities of Rep protein, which down-regulates its own expression and reverses cellular immortalization. This invention provides packaging systems and processes for packaging AAV vectors that efficiently circumvent these problems by replacing the AAV p5 promoter with a heterologous promoter and that allow for substantially increased packaging efficiency.

15 Claims, 6 Drawing Sheets

OTHER PUBLICATIONS

Carter, B.J., et al., "AAV DNA Replication, integration, and genetics" *CRC Handbook of Parvoviruses*, Tijssen, P., ed., (1989) CRC Press, Inc., Boca Raton, FL., vol. I, Chapter 11, pp. 169–226.

Berns, K.I., "Parvoviridae and their replication" *Fields Virology*, Fields, B.N., et al., eds. (1990) Raven Press, New York, NY., vol. 2, pp. 1743–1763.

Dialog™ Computer Abstract (Biosys File) of Kotin, R.M., et al., "Organization of adeno–associated virus DNA in latently infected detroit 6 cells" *Virology* (1989) 170(2):460–467.

Kotin, R.M., et al., "Site specific integration by adeno–associated virus" *Proc. Natl. Acad. Sci. USA* (1990) 87:2211–2215.

Dialog™ Computer Abstract (Biosys File) of Samulski, R.J., et al., "Targeted integration of adeno–associated virus AAV into human chromosome 19" *EMBO J.* (1991) 10(12):3941–3950.

Dialog™ Computer Abstract (Biosys File) of Srivastava, A., et al., "Nucleotide sequence and organization of the adeno–associated virus 2 genome" *J. Virol.* (1983) 45(2):555–564.

Hermonat, P.L., et al., "Genetics of adeno–associated virus: Isolation and preliminary characterization of adeno–associated virus type 2 mutants" *J. Virol.* (1984) 51(2):329–339.

Tratschin, J.D., et al., "Genetic analysis of adeno–associated virus: Properties of deletion mutants constructed in vitro and evidence for an adeno–associated virus replication function" *J. Virol.* (1984) 51(3):611–619.

Laughlin, C.A., et al., "Spliced adenovirus–associated virus RNA" *Proc. Natl. Acad. Sci. USA* (1979) 76(11):5567–5571.

Tratschin, J.D., et al., "Negative and positive regulation in trans of gene expression from adeno–associated virus vectors in mammalian cells by a viral rep gene product" *Mol. Cell. Biol.* (1986) 6(8):2884–2894.

Labow, M.A., et al., "Adeno–associated virus gene expression inhibits cellular transformation by heterologous genes" *Mol. Cell. Biol.* (1987) 7(4):1320–1325.

Khleif, S.N., et al., "Inhibition of cellular transformation by the adeno–associated virus rep gene" *Virology* (1991) 181:738–741.

Mendelson, E., et al., "Expression and rescue of a nonselected marker from an integrated AAV vector" *Virology* (1988) 166:154–165.

Samulski, R.J., et al., "Cloning of adeno–associated virus into pBR322: Rescue of intact virus from the recombinant plasmid in human cells" *Proc. Natl. Acad. Sci. USA* (1982) 79:2077–2081.

Laughlin, C.A., et al., "Cloning of infectious adeno–associated virus genomes in bacterial plasmids" *Gene* (1983) 23:65–73.

Senapathy, P., et al., "Molecular cloning of adeno–associated virus variant genomes and generation of infectious virus by recombination in mammalian cells" *J. Biol. Chem.* (1984) 259(7):4661–4666.

Tratschin, J.D., et al., "A human parvovirus, adeno–associated virus, as a eucaryotic vector: Transient expression and encapsidation of the procaryotic gene for chloramphenicol acetyltransferase" *Mol. Cell. Biol.* (1984) 4(10):2072–2081.

Hermonat, P.L., et al., "Use of adeno–associated virus as a mammalian DNA cloning vector: Transduction of neomycin resistance into mammalian tissue culture cells" *Proc. Natl. Acad. Sci. USA* (1984) 81:6466–6470.

Tratschin, J.D., et al., "Adeno–associated virus vector for high-frequency integration, expression, and rescue of genes in mammalian cells" *Mol. Cell. Biol.* (1985) 5(11):3251–3260.

McLaughlin, S.K., et al., "Adeno–associated virus general transduction vectors: Analysis of proviral structures" *J. Virol.* (1988) 62(6):1963–1973.

Lebkowski, J.S., et al., "Adeno–associated virus: a vector system for efficient introduction and integration of DNA into a variety of mammalian cell types" *Mol. Cell. Biol.* (1988) 8(10):3988–3996.

Carter, B.J., et al., "Parvoviruses as vectors" *CRC Handbook of Parvoviruses*, Tijssen, P., ed., (1989) CRC Press, Inc., Boca Raton, FL., vol. II, Chapter 18, pp. 247–284.

Samulski, R.J., et al., "A recombinant plasmid from which an infectious adeno–associated virus genome can be excised in vitro and its use to study viral replication" *J. Virol.* (1987) 61(10):3096–3101.

Samulski, R.J., et al., "Helper–free stocks of recombinant adeno–associated viruses: Normal integration does not require viral gene expression" *J. Virol.* (1989) 63(9):3822–3828.

LaFace, D., et al., "Gene transfer into hematopoietic progenitor cells mediated by an adeno–associated virus vector" *Virology* (1988) 162:483–486.

Srivastava, C.H., et al., "Construction of a recombinant human parvovirus B19: Adeno–associated virus 2 (AAV) DNA inverted terminal repeats are functional in an AAV–B19 hybrid virus" *Proc. Natl. Acad. Sci. USA* (1989) 86:8078–8082.

Chatterjee, S., et al., "Transduction of intracellular resistance to HIV production by an adeno–associated virus–based antisense vector" *Vaccines 91* (1991) Cold Spring Harbor Laboratory Press, pp. 85–90.

Wong, K.K., et al., "Restriction of HSV-1 production in cell lines transduced with an antisense viral vector targeting the ICP4 gene" *Vaccines 91* (1991) Cold Spring Harbor Laboratory Press, pp. 183–189.

Chatterjee, S., et al., "Dual–target inhibition of HIV–1 in vitro by means of an adeno–associated virus antisense vector" *Science* (1992) 258:1485–1488.

Muro–Cacho, C.A., et al., "Gene transfer in human lymphocytes using a vector based on adeno–associated virus" *J. Immunol.* (1992) 11:231–237. An author proof was previously enclosed.

Antoni, B.A., et al., "Adeno–associated virus rep protein inhibits human immunodeficiency virus type 1 production in human cells" *J. Virol.* (1991) 65(1):396–404.

Kotin, R.M., et al., "Characterization of a preferred site on human chromosome 19q for integration of adeno–associated virus DNA by non–homologous recombination" *EMBO J.* (1992) 11(13):5071–5078.

Labow, M.A., et al., "Positive and negative autoregulation of the adeno–associated virus type 2 genome" *J. Virol.* (1986) 60(1):251–258.

Vincent, K.A., et al., "Replication and packaging of HIV envelope genes in a novel adeno–associated virus vector system" *Vaccines 90* (1990) Cold Spring Harbor Laboratory Press, pp. 353–359.

Labow et al., "The adeno–associated virus rep gene inhibits replication of an adeno–associated virus/simian virus 40 hybrid genome in cos–7 cells" *J. Virol.* (1988) pp. 1705–1912.

Rittner et al., "Adeno–associated virus type 2–mediated inhibition of human immunodeficiency virus type 1 (HIV–1) replication: involvement of p78$^{rep}$/p68$^{rep}$ and the HIV–1 long terminal repeat" *J. Gen. Virol.* (1992) 73:2977–2981.

Yang et al., "Characterization of cell lines that inducibly express the adeno–associated virus rep proteins" *J. Virol.* (1994) 68:4847–4856.

Blacklow, "Adeno–associated viruses of humans" *Parvoviruses and Human Disease* (1988) J.R. Pattison, ed., Chapter 11, pp. 165–174.

Rose, "Parvovirus reproduction" *Comprehensive Virology 3* (1974) H. Fraenkel–Conrat et al., eds., Chapter 1, pp. 1–60.

Rich et al., "Effect of deleting the R domain on CFTR–generated chloride channels" *Science* (1991) 253:205–207.

Arispe et al., "Intrinsic anion channel activity of the recombinant first nucleotide binding fold domain of the cystic fibrosis transmembrane regulator protein" *Proc. Natl. Acad. Sci. USA* (1992) 89:1539–1543.

Sheppard et al., "The amino–terminal portion of CFTR forms a regulated Cl$^-$ channel" *Cell* (1994) 76:1091–1098.

GENERATION OF HIGH TITERS OF RECOMBINANT AAV VECTORS

CROSS-REFERENCE TO RELATED APPLICATIONS

This application is the U.S. National phase of PCT Application No. PCT/US94/12587, filed 3 Nov. 1994; which is a continuation-in-part of U.S. patent application Ser. No. 08/149,332, filed 9 Nov. 1993, now abandoned.

TECHNICAL FIELD OF THE INVENTION

This invention relates to gene therapy, and more specifically to materials and methods used for the generation of high titers of recombinant AAV vectors for use in gene therapy procedures.

BACKGROUND OF THE INVENTION

AAV vectors may have utility for gene therapy but heretofore a significant obstacle has been the inability to generate sufficient quantities of such recombinant vectors in amounts that would be clinically useful for human gene therapy application. This is a particular problem for in vivo applications such as direct delivery to the lung.

Adeno-associated virus (AAV) vectors are among a small number of recombinant virus vector systems which have been shown to have utility as in vivo gene transfer agents (reviewed in Carter, 1992, *Current Opinion in Biotechnology*, 3:533–539; Muzcyzka, 1992, *Curr. Top. Microbiol. Immunol.* 158:97–129) and thus are potentially of great importance for human gene therapy. AAV vectors are capable of high-frequency stable DNA integration and expression in a variety of cells including cystic fibrosis (CF) bronchial and nasal epithelial cells (Flotte et al., 1992a, *Am. J. Respir. Cell Mol. Biol.* 7:349–356; Egan et al., 1992, *Nature*, 358:581–584; Flotte et al., 1993a, *J. Biol. Chem.* 268:3781–3790; Flotte et al., 1993b, *Proc. Natl. Acad. Sci. USA*, in press), human bone marrow-derived erythroleukemia cells (Walsh et al., 1992, *Proc. Natl. Acad. Sci. USA*, 89:7257–7261), and several others. AAV may not require active cell division for stable expression which would be a clear advantage over retroviruses, especially in tissue such as the human airway epithelium where most cells are terminally differentiated and non-dividing.

AAV is a defective parvovirus that grows only in cells in which certain functions are provided by a co-infecting helper virus (see FIG. 1). General reviews of AAV may be found in Carter, 1989, *Handbook of Parvoviruses*, Vol. I, pp. 169–228, Carter, 1989, *Handbook of Parvoviruses*, Vol. I, pp. 169–228, Berns, 1990, *Virology*, pp. 1743–1764, Raven Press, (New York). Examples of co-infecting viruses that provide helper functions for AAV growth and replication are adenoviruses, herpesviruses and in some cases poxviruses such as vaccinia. The nature of the helper function is not known but appears to be some indirect effect of the helper virus which renders the cell permissive for AAV replication. This concept is supported by the observation that in certain cases AAV replication may occur at a low level of efficiency in the absence of helper virus co-infection if the cells are treated with agents that are either genotoxic or that disrupt the cell cycle.

Although AAV may replicate to a limited extent in the absence of helper virus in certain unusual conditions, as noted above, the more general result is that infection of cells with AAV in the absence of helper functions results in integration of AAV into the host cell genome. The integrated AAV genome may be rescued and replicated to yield a burst of infectious progeny AAV particles if cells containing an integrated AAV provirus are superinfected with a helper virus such as adenovirus. Because the integration of AAV appears to be an efficient event, this suggested that AAV would be a useful vector for introducing genes into cells for stable expression for uses such as human gene therapy. More recent results (Kotin & Berns, 1989, *Virology* 170:460–467; Kotin et al., 1990, *Proc. Natl. Acad. Sci. USA*, 87:2211–2215; Samulski et al., 1991, *EMBO J.* 10:3941–3950) have suggested that AAV may exhibit some preference for integration at a site on human chromosome 19 but the generality and mechanism of this phenomenon has not been elucidated fully.

AAV has a very broad host range with neither any obvious species or tissue specificity and will replicate in virtually any cell line of human, simian or rodent origin provided an appropriate helper is present. AAV is ubiquitous and has been isolated from a wide variety of animal species including most mammalian and several avian species.

AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector because most of the other viral systems proposed for this application such as retroviruses, adenoviruses, herpesviruses, or poxviruses are disease-causing viruses.

AAV particles are comprised of a protein capsid having three capsid proteins, VP1, VP2, and VP3, and enclosing a DNA genome. The AAV DNA genome is a linear single-stranded DNA molecule having a molecular weight of about $1.5 \times 10^6$ daltons or approximately 4680 nucleotides long. Strands of either complementary sense, "plus" or "minus" strands, are packaged into individual particles but each particle has only one DNA molecule. Equal numbers of AAV particles contain either a plus or minus strand. Either strand is equally infectious and replication occurs by conversion of the parental infecting single strand to a duplex form and subsequent amplification of a large pool of duplex molecules from which progeny single strands are displaced and packaged into capsids. Duplex or single-strand copies of AAV genomes inserted into bacterial plasmids or phagemids are infectious when transfected into adenovirus-infected cells, and this has allowed the study of AAV genetics and the development of AAV vectors. The replication cycle of AAV is diagrammed in FIG. 1.

The AAV2 genome has one copy of the 145-nucleotide-long ITR (inverted terminal repeat) of each end and a unique sequence region of about 4470 nucleotides long (Srivastava et al., 1983, *J. Virol,* 45:555–564) that contains two main open reading frames for the rep and cap genes (Hermonat et al., *J. Virol.* 51:329–339; Tratschin et al., 1984a, *J. Virol.,* 51:611–619). The unique region contains three transcription promoters $p_5$, $p_{19}$, and $p_{40}$ (Laughlin et al., 1979, *Proc. Natl. Acad. Sci. USA,* 76:5567–5571) that are used to express the rep and cap genes. The ITR sequences are required in cis and are sufficient to provide a functional origin of replication (ori) and also are sufficient to provide signals required for integration into the cell genome as well as for efficient excision and rescue from host cell chromosomes or from recombinant plasmids. In addition it has been shown that the ITR can function directly as a transcription promoter in an AAV vector (Flotte et al., 1993, vide supra).

The rep and cap genes are required in trans to provide functions for replication and encapsidation of vital genome respectively. The rep gene is expressed from two promoters, $p_5$ and $p_{19}$. Transcription from $p_5$ yields an unspliced 4.2 kb mRNA which encodes a protein, Rep78, and a spliced 3.9 kb mRNA which encodes a protein, Rep68. Transcription from $p_{19}$ yields an unspliced mRNA which encodes Rep52 and a spliced 3.3 kb mRNA which encodes Rep40. Thus, the four Rep proteins all comprise a common internal region sequence but differ with respect to their amino and carboxyl terminal regions. Only Rep78 and Rep68 are required for AAV duplex DNA replication, but Rep52 and Rep40 appear to be needed for progeny, single-strand DNA accumulation. Mutations in Rep78 and Rep68 are phenotypically Rep⁻ whereas mutations affecting only Rep52 and Rep40 are Rep⁺ but Ssd⁻. Rep68 and Rep78 bind specifically to the hairpin conformation of the AAV ITR and possess several enzyme activities required for resolving replication at the AAV termini. Rep52 and Rep40 have none of these properties.

The Rep proteins, primarily Rep78 and Rep68 exhibit several pleiotropic regulatory activities including positive and negative regulation of AAV genes and expression from some heterologous promoters, as well as inhibitory effects on cell growth (Tratschin et al., 1986, *Mol. Cell. Biol.* 6:2884–2894; Labow et al., 1987, *Mol. Cell. Biol.*, 7:1320–1325¹Khleif et al., *Virology*, 181:738–741). The AAV $p_5$ promoter is negatively autoregulated by Rep78 or Rep68 (Tratschin et al., 1986, *Mol. Cell. Biol.* 6:2884–2894). Because of the inhibitory effects of expression of rep on cell growth, constitutive expression of rep in cell lines has not been readily achieved. For example, Mendelson et al. (1988, *Virology*, 166:154–165) reported a very low level expression of some Rep proteins in certain cell lines after stable integration of AAV genomes.

The proteins VP1, VP2, and VP3 all share a common overlapping sequence but differ in that VP1 and VP2 contain additional amino terminal sequence. All three are coded from the same cap gene reading frame expressed from a spliced 2.3 kb mRNA transcribed from the $p_{40}$ promoter. VP2 and VP3 are generated from the same mRNA by use of alternate initiation codons. VP1 is coded from a minor mRNA using 3' donor site that is 30 nucleotides upstream from the 3' donor used for the major mRNA that encodes VP2 and VP3. VP1, VP2, and VP3 are all required for capsid production. Mutations which eliminate all three proteins (Cap⁻) prevent accumulation of single-strand progeny AAV DNA whereas mutations in the VP1 amino-terminus (Lip⁻, Inf⁻) permit single-strand production but prevent assembly of stable infectious particles.

The genetic analysis of AAV that was described above was based upon mutational analysis of AAV genomes that were molecularly cloned into bacterial plasmids. In early work, molecular clones of infectious genomes of AAV were constructed by insertion of double-strand molecules of AAV into plasmids by procedures such as GC tailing (Samulski et al., 1982, *Proc. Natl. Acad. Sci. USA*, 79:2077–2081), addition of synthetic linkers containing restriction endonuclease (Laughlin et al., 1983, *Gene*, 23:65–73) or by direct, blunt-end ligation (Senapathy & Carter, 1984, *J. Biol. Chem.*, 259:4661–4666). It was then shown that transfection of such AAV recombinant plasmids into mammalian cells that were also infected with an appropriate helper virus, such as adenovirus, resulted in rescue and excision of the AAV genome free of any plasmid sequence and replication of the rescued genome and generation of a yield of progeny infectious AAV particles (see FIG. 1). This provided the basis for performing genetic analysis of AAV as summarized above and permitted construction of AAV transducing vectors.

Based on the genetic analysis, the general principles of AAV vector construction were defined as reviewed recently (Carter, 1992, *Current Opinions in Biotechnology*, 3:533–539; Muzyczka, 1992, *Current Topics in Microbiology and Immunology*, 158:97–129). AAV vectors are constructed in AAV recombinant plasmids by substituting portions of the AAV coding sequence with foreign DNA to generate a vector plasmid. In the vector plasmid, the terminal (ITR) portions of the AAV sequence must be retained intact because these regions are required in cis for several functions including excision from the plasmid after transfection, replication of the vector genome and integration and rescue from a host cell genome. The vector can then be packaged into an AAV particle to generate an AAV transducing virus by transfection of the vector plasmid into cells that are infected by an appropriate helper virus such as adenovirus or herpesvirus. In order to achieve replication and encapsidation of the vector genome into AAV particles, the vector plasmid must be complemented for any AAV functions required in trans, namely rep and cap, that were deleted in construction of the vector plasmid.

There are at least two desirable features of any AAV vector that is designed for use in human gene therapy. First, the transducing vector must be generated at sufficiently high titers that it is practicable as a delivery system. This is especially important for gene therapy stratagems aimed at in vivo delivery of the vector. It is likely that for many desirable applications of AAV vectors, such as treatment of cystic fibrosis by direct in vivo delivery to the airway, the required dose of transducing vector may be in excess of $10^{10}$. Secondly, the vector preparations must be free of wild-type AAV virus. The attainment of high titers of AAV vectors has been difficult for several reasons including preferential encapsidation of wild-type AAV genomes if they are present or generated by recombination, and the inability to generate sufficient complementing functions such as rep or cap. Useful cell lines expressing such complementing functions have not been generated, in part, because of several inhibitory functions of the rep gene.

The first AAV vectors that were described contained foreign reporter genes such as neo or cat or dhfr that were expressed from AAV transciption promoters or an SV40 promoter (Tratschin et al., 1984b, *Mol. Cell. Biol.* 4:2072–2081; Hermonat & Muzyczka, 1984, *Proc. Natl. Acad. Sci. USA*, 81:6466–6470; Tratschin et al., 1985, *Mol. Cell. Biol.* 5:3251–3260; McLaughlin et al., 1988, *J. Virol.*, 62:1963–1973; Lebkowski et al., 1988 *Mol. Cell. Biol.*, 7:349–356). These vectors were packaged into AAV-transducing particles by co-transfection into adenovirus-infected cells together with a second packaging plasmid that contained the AAV rep and cap genes expressed from the natural wild-type AAV transciption promoters. In an attempt to prevent packaging of the packaging plasmid into AAV particles several approaches were taken. In some cases, (Hermonat & Muzyczka, 1984; McLaughlin et al., 1988) the packaging plasmid had inserted a large region of bacteriophage lambda DNA within the AAV sequence to generate an oversized genome that could not be packaged. In other cases, (Tratschin et al., 1984b; Tratschin et al., 1985, Lebkowski et al., 1988), the packaging plasmid had deleted the ITR regions of AAV in order that it could not be excised and replicated and thus could not be packaged. All of these approaches failed to prevent generation of particles containing wild-type AAV DNA and also failed to generate effective high titere of AAV transducing particles. Indeed titers of not more than $10^4$ ml were cited by Hermonat & Muzyczka, 1984. The production of wild-type AAV particles in these studies was probably due to the presence of overlapping homology between AAV sequences present in the vector and packaging plasmids. It was shown by Senapathy and Carter (1984, *J. Biol. Chem.* 259:4661–4666) that the degree of recombination in such a system is approximately equivalent to the degree of sequence overlap. It was suggested in a review of the early work (Carter 1989, *Handbook of Parvoviruses*, Vol. II, pp. 247–284, CRC Press, Boca Raton, Fla.) that titers of $10^6$ per ml might be obtained, but this was based on the above-cited studies in which large amounts of wild-type AAV contaminated the vector preparation. Such vector preparations containing wild-type AAV are not useful human gene therapy. Furthermore, these early vectors exhibited low transduction efficiencies and did not transduce more than 1 or 2% of cells in cultures of various human cell lines even though the vectors were supplied at multiplicities of up to 50,000 particles per cell. This may have reflected in part the contamination with wild-type AAV particles and the presence of the AAV rep gene in the vector. Furthermore, Samulski et al. (1989, *J. Virol.* 63:3822–3828) showed that the presence of wild-type AAV significantly enhanced the yield of packaged vector. Thus, in packaging systems where the production of wild-type AAV is eliminated, the yield of packaged vector may actually be decreased. Nevertheless, for use in any human clinical application it will be essential to eliminate production of wild-type AAV.

Additional studies (McLaughlin et al., 1988; Lebkowski et al., 1988) to generate AAV vectors which did not contain the AAV rep or cap gene still met with generation of wild-type AAV and still produced very low transduction frequencies on human cell lines. Thus, McLaughlin et al., 1988 reported that AAV rep$^-$cap$^-$ vectors containing the neo gene packaged with the same packaging plasmid used earlier by Hermonat & Muzyczka (1984) still contained wild-type AAV. As a consequence it was only possible to use this virus at a multiplicity of 0.03 particles per cell (i.e., 300 infectious units per 10,000 cell) to avoid double hits with vector and wild-type particles. When the experiment was done in this way, by infecting 32,000 cells with 1000 infectious units, an average of 800 geneticin-resistant colonies was obtained. Although this was interpreted as demonstrating the virus was capable of yielding a transduction frequency of 80%, in fact only 2.5% of the cells were transduced. Thus the effectively useful titer of this vector was limited. Furthermore, this study did not demonstrate that the actual titer of the vector preparation was any higher than those obtained previously by Hermonat & Muzyczka (1984). Similarly, Lebkowski et al., 1988, packaged AAV vectors which did not contain either a rep or cap gene and used an ori$^-$ packaging plasmid pBa1A identical to that used earlier by Tratschin et al., (1984b, 1985) and reported transduction frequencies that were similarly low, in that for several human cell lines not more than 1% of the cells could be transduced to geneticin resistance even with their most concentrated vector stocks. Lebkowski et al., (1988) did not report the actual vector titers in a meaningful way but the biological assays showing not more than 1% transduction frequency when $5\times10^6$ cells were exposed to three ml of vector preparation indicates that the titer was less than $2\times10^4$. Also, the pBa1 packaging plasmid contains overlapping homology with the ITR sequence in the vector and leads to generation by recombination of wild-type AAV.

Laface et al., (1988) used the same vector as that used by Hermonat & Muzyczka (1984) prepared in the same way and obtained a transduction frequency of 1.5% in murine bone marrow cultures again showing very low titer.

Samulski et al., (1987, *J. Virol.*, 61:3096–3101) constructed a plasmid called pSub201 which was an intact AAV genome in a bacterial plasmid but which had a deletion of 13 nucleotides at the extremity of each ITR and thus was rescued and replicated less efficiently than other AAV plasmids that contained the entire AAV genome. Samulski et al. (1989, *J. Virol.*, 63:3822–3828) constructed AAV vectors based on pSub201 but deleted for rep and cap and containing either a hyg or neo gene expressed from an SV40 early gene promoter. They packaged these vectors by co-transfection with a packaging plasmid called pAAV/Ad which consisted of the entire AAV nucleotide sequence from nucleotide 190 to 4490 enclosed at either end with one copy of the adenovirus ITR. In this packaging plasmid the AAV rep and cap genes were expressed from the natural AAV promoters $p_5$, $p_{19}$ and $p_{40}$. The function of the adenovirus ITR in pAAV/Ad was thought to be to enhance the expression level of AAV capsid proteins. However, rep is expressed from its homologous promoter and is negatively regulated and thus its expression is limited. Using their encapsidation system Samulski et al., 1989, generated AAV vector stocks that were substantially free of wild-type AAV but had transducing titers of only $3\times10^4$ hygromycin-resistant units per ml of supernatant. When a wild-type AAV genome was used in the packaging plasmid the titer of the AAV vector prep was increased to $5\times10^4$. The low titer produced in this system thus appears to have been due in part to the defect in the ITR sequences of the basic pSub201 plasmid used for vector construction and in part due to limiting expression of AAV genes from pAAV/Ad. In an attempt to increase the titer of the AAVneo vector preparation, Samulski et al., 1989, generated vector stocks by transfecting, in bulk, thirty 10-cm dishes of 293 cells and concentrating the vector stock by banding in CsCl. This produced an AAVneo vector stock containing a total of $10^8$ particles as measured by a DNA dot-blot hybridization assay. When this vector stock was used at multiplicities of up to 1,000 particles per cell, a transduction frequency of 70% was obtained. This suggests that the particle-to-transducing ratio is about 500 to 1,000 particles since at the ratio of one transducing unit per cell the expected proportion of cells that should be transduced is 63% according to the Poisson distribution.

Although the system of Samulski et al., 1989, using the vector plasmid pSub201 and the packaging plasmid pAAV/Ad did not have overlapping AAV sequence homology between the two plasmids, there is overlapping homology at the XbaI sites and recombination of these sites leads to generation of complete wild-type AAV. That is, although overlapping homology of AAV sequence is not present, the complete AAV sequence is contained within the two plasmids, and thus recombination can generate wild-type AAV, which is undesirable. That this class of recombination occurs in AAV plasmids was shown by Senapathy & Carter (1984, *J. Biol. Chem.* 259:4661–4666). Therefore, because of the problems of low titer and ability to generate wild-type recombinants, the system described by Samulski et al., 1989, does not have utility for human gene therapy.

Several other reports have described AAV vectors. Srivastava et al., (1989, *Proc. Natl. Acad. Sci. USA*, 86:8078–8082) described an AAV vector based on the pSub201 plasmid of Samulski et al., (1987), in which the coding sequences of AAV were replaced with the coding sequences of another parvovirus, B19. This vector was packaged into AAV particles using the pAAV/Ad packaging plasmid and generated a functional vector, but titers were not reported. This system was based on pSub281 and thus suffers from the defect described above for this plasmid. Second, the vector and the packaging plasmid both contained overlapping AAV sequences (the ITR regions) and thus recombination to give contaminating wild-type virus is highly likely.

Chatterjee et al. (1991, *Vaccines* 91, Cold Spring Harbor Laboratory Press, pp. 85–89), Wong et al. (1991 *Vaccines* 91, Cold Spring Harbor Laboratory Press, pp. 183–189), and Chatterjee et al. (1992, *Science*, 258:1485–1488) describe AAV vectors designed to express antisense RNA directed against infectious viruses such as HIV or Herpes simplex virus. However, these authors did not report any titers of their AAV vector stocks. Furthermore, they packaged their vectors using and Ori⁻ packaging plasmid analogous to that used by Tratschin et al. (1984b, 1985) containing the BalA fragment of the AAV genome and therefore their packaging plasmid contained AAV vector sequences that have homology with AAV sequences that were present in their vector constructs. This will also lead to generation of wild-type AAV. Thus, Chatterjee et al., and Wong et al., used a packaging system known to give only low titer and which can lead to generation of wild-type AAV genomes because of the overlapping homology in the vector and packaging sequences.

Other reports have described the use of AAV vectors to express genes in human lymphocytes (Muro-Cacho et al., 1992, *J. Immunotherapy*, 11:231–237) or a human erythroid leukemia cell line (Walsh et al., 1992, *Proc. Natl. Acad. Sci. USA*, 89:7257–7261) with vectors based on the pSub201 vector plasmid and pAAV/Ad packaging plasmid. Again, titers of vector stocks were not reported and were apparently low because a selective marker gene was used to identify those cells that had been successfully transduced with the vector.

Transduction of human airway epithelial cells, grown in vitro from a cystic fibrosis patient, with an AAV vector expressing the selective marker gene neo from the AAV $p_5$ promoter was reported (Flotte et al., 1992, *Am. J. Respir. Cell. Mol. Biol.* 7:349–356). In this study the AAVneo vector was packaged into AAV particles using the pAAV/Ad packaging plasmid. Up to 70% of the cells in the culture could be transduced to geneticin resistance and the particle-to-transducing ratio was similar to that reported by Samulski et al., (1989). Thus to obtain transduction of 70% of the cells, a multiplicity of up to several hundred vector particles per cell was required. Transduction of human airway epithelial cells in in vitro culture using an AAV transducing vector that expressed the CFTR gene from the AAV ITR promoter showed that the cells could be functionally corrected for the electrophysiological defect in chloride channel function that exists in cells from cystic fibrosis patients (Egan et al., *Nature*, 1992, 358:581–584; Flotte et al., *J. Biol. Chem.* 268:3781–3790).

The above-cited studies suggest that AAV vectors may have potential utility as vectors for treatment of human disease by gene therapy. However, the ability to generate sufficient amounts of AAV vectors has been a severe limitation on the development of human gene therapy using AAV vectors. One aspect of this limitation has also resulted in the prior absence of any studies using AAV vectors in in vivo animal models. This is generally a reflection of the difficulty associated with generating sufficient amounts of AAV vector stocks having a high enough titer to be useful in analyzing in vivo delivery and gene expression. One of the limiting factors for AAV gene therapy has been the relative inefficiency of the vector packaging systems that have been used. Because of the lack of cell lines expressing the AAV trans complementing functions, such as rep and cap, packaging of AAV vectors has been achieved in adenovirus-infected cells by co-transfection of a packaging plasmid and a vector plasmid. The efficiency of this process may be limited by the efficiency of transfection of each of the plasmid constructs, and by the level of expression of Rep proteins from the packaging plasmids described to date. Each of these problems appears to relate to the biological activities of the AAV Rep proteins. In addition, and as noted above, all of the packaging systems described above have the ability to generate wild-type AAV by recombination.

The lack of cell lines stably expressing functional Rep apparently reflects a cytotoxic or cytostatic function of Rep as shown by the inhibition by Rep of neo-resistant colony formation (Labow et al., 1987; Trempe et al., 1991). This also appears to relate to the tendency of Rep to reverse the immortalized phenotype in cultured cells, which has made the production of cell lines stably expressing functional Rep extremely difficult. Several attempts to generate cell lines expressing Rep have been made. Mendelson et al., (1988, *Virology*, 166:154–165) reported obtaining in one cell line some low level expression of AAV Rep52 protein but no Rep78 or Rep68 protein after stable transfection of HeLa or 293 cells with plasmids containing an AAV rep gene. Because of the absence of Rep78 and Rep68 proteins, vector could not be produced in the cell line. Another cell line made a barely detectable amount of Rep78 which was nonfunctional.

Vincent et al. (1990, *Vaccines* 90, Cold Spring Harbor Laboratory Press, pp. 353–359) attempted to generate cell lines containing the AAV rep and cap genes expressed from the normal AAV promoters, but these attempts were not successful either because the vectors were contaminated with a 100-fold excess of wild-type AAV particles or because the vectors were produced at only very low titers of less than $4 \times 10^3$.

In an alternate approach, Lebkowski et al. (U.S. Pat. No. 5,173,414, issued Dec. 22, 1992) constructed cell lines containing AAV vectors in an episomal plasmid. These cell lines could then be infected with adenovirus and transfected with the trans complementing AAV functions rep and cap to generate preparations of AAV vector. It is claimed that this allows higher titers of AAV stocks to be produced. However, in the examples shown, the only information relative to titer that is shown is that one human cell line, K562, could be transduced at efficiencies of only 1% or less, which does not indicate high titer production of any AAV vector. In this system the vector is carried as an episomal (unintegrated construct), and it is stated that integrated copies of the vector are not preferred.

The approach to packaging of AAV vectors described by Lebkowski et al., 1992, has several undesirable aspects. First, maintaining the vector as an unintegrated, high copy number episomal plasmid in a cell line is not desirable because the copy number per cell cannot be rigorously controlled and episomal DNA is much more likely to undergo rearrangement leading to production of defective vectors. Secondly, in this system, the vector must still be packaged by infecting the cell line with adenovirus and introducing a plasmid containing the AAV rep and cap genes. The plasmid used by Lebkowski et al., 1992, again was pBal which, as noted above, has overlapping homology with the vector ITR sequences and will result in generation of wild-type AAV. Third, in the pBal packaging plasmid used by Lebkowski et al., 1988, 1992, the rep gene is expressed off its homologous $p_5$ promoter and is thus negatively autoregulated and therefore rep expression is likely to be limited.

The problem of suboptimal levels of rep expression after plasmid transfection may relate to another biological activity of these proteins. There is evidence (Tratschin et al., 1986,

*Mol. Cell. Biol.* 6:2884–2894) that AAV-Rep proteins down-regulate their own expression from the AAV-p$_5$ promoter which has been used in all of the previously described packaging constructs such as pAAV/Ad (Samulski et al., 1989) or pBal (Lebkowski et al., 1988, 1992).

SUMMARY OF THE INVENTION

One of the basic challenges for gene therapy has been the development of strategies for transduction of cells and tissues which cannot be easily manipulated ex vivo or which are not actively dividing. AAV vectors can achieve in vivo gene transfer in the respiratory tract, for example, but high titers are critical so as to allow for the delivery of sufficiently high multiplicity of vector in as small a volume as possible. This makes optimal packaging methodology of central importance in determining the feasibility of an AAV-based gene therapy. Stable, helper-free AAV packaging cell lines have been elusive, mainly due to the activities of Rep protein, which down-regulates its own expression and reverses cellular immortalization. The approaches described in this invention effectively circumvent these problems and have allowed for substantial improvements in packaging efficiency.

The use of an HIV-LTR promoter to express high levels of AAV-Rep proteins has been reported elsewhere (Antoni et al., 1991), but the application of this expression system to packaging of recombinant AAV vectors is a new development. In fact, it has not been previously demonstrated that the levels of Rep expression are limiting in the co-transfection AAV-vector packaging process. The fact that a 10-fold increase in packaging titer was achieved by increasing Rep expression provides direct evidence that levels of Rep are limiting in this circumstance. The fact that pARtat co-transfection did not further increase the efficiency of packaging may indicate either that (1) the level of expression from the HIV promoter in 293 cells was maximized even in the absence of tat or (2) that the levels of Rep achieved with pRS5 alone were sufficient to ensure that Rep expression was no longer limiting for packaging efficiency. It would now be obvious that other non-AAV promoters can be used to generate Rep in packaging plasmids analogous to pRS5.

Likewise, the phenomenon of rescue of integrated recombinant AAV genomes is known (Tratschin et al., 1985; Flotte et al., 1993a), but has never before been applied to produce a vector-producing cell line as has been described here.

The overall packaging efficiency of the pRS5-vector cell line system was at least $10^4$ particles per packaging cell, which will be more than sufficient to allow for the production of clinical grade AAV recombinant vector reagents. Wild-type AAV generation has not been observed with this method, which is an additional advantage over most co-transfection methods. These improvements render feasible the production of clinical grade AAV recombinant vectors for use in gene therapy.

Described herein are procedures and constructs which allow the production of high titers of AAV vectors in the absence of the generation of wild-type AAV.

Accordingly, one embodiment of the invention is a process for the generation of high titers of AAV recombinant vectors comprising:

(a) providing cells containing at least one intact copy of a stably integrated recombinant AAV vector, wherein the AAV vector is comprised of AAV inverted terminal repeat (ITR) regions and a transcription promoter operably linked to a target polynucleotide, and wherein the expression of the rep gene is limiting in said cells;

(b) providing an AAV packaging plasmid that allows expression of the product of the rep gene, wherein in the plasmid the rep gene is operably linked to a heterologous promoter, and wherein the packaging plasmid lacks overlapping homology with AAV sequences in the vector in the cell provided in (a);

(c) inserting the AAV packaging plasmid into the cell and incubating the cell under conditions that allow replication of AAV; and (d) isolating recombinant AAV vectors produced in step (c).

Included within this embodiment are processes wherein the promoter in the packaging plasmid to which Rep is operably linked is HIV-LTR, and within those processes wherein the packaging plasmid is pRS5.

Also included within this embodiment are processes wherein the target polynucleotide encodes a polypeptide that can function as a cystic fibrosis transmembrane conductance regulator (CFTR).

Another embodiment of the invention is a packaging system for the generation of high titers of AAV recombinant vectors comprising:

(a) cells containing at least one intact copy of a stably integrated recombinant AAV vector, wherein the AAV vector is comprised of AAV inverted terminal repeat (ITR) regions and a transcription promoter operably linked to a target polynucleotide, and wherein the expression of the rep gene is limiting in said cells; and (b) an AAV packaging plasmid that allows expression of the product of the rep gene, wherein in the plasmid the rep gene is operably linked to a heterologous promoter, and wherein the packaging plasmid lacks overlapping homology with AAV sequences in the vector in the cell provided in (a).

Still another embodiment of the invention is a packaging plasmid for use in the production of the generation of high titers of AAV recombinant vectors that allows expression of the product of the rep gene, wherein the plasmid is comprised of rep gene operably linked to a heterologous promoter.

DETAILED DESCRIPTION OF THE INVENTION

Figure 1:
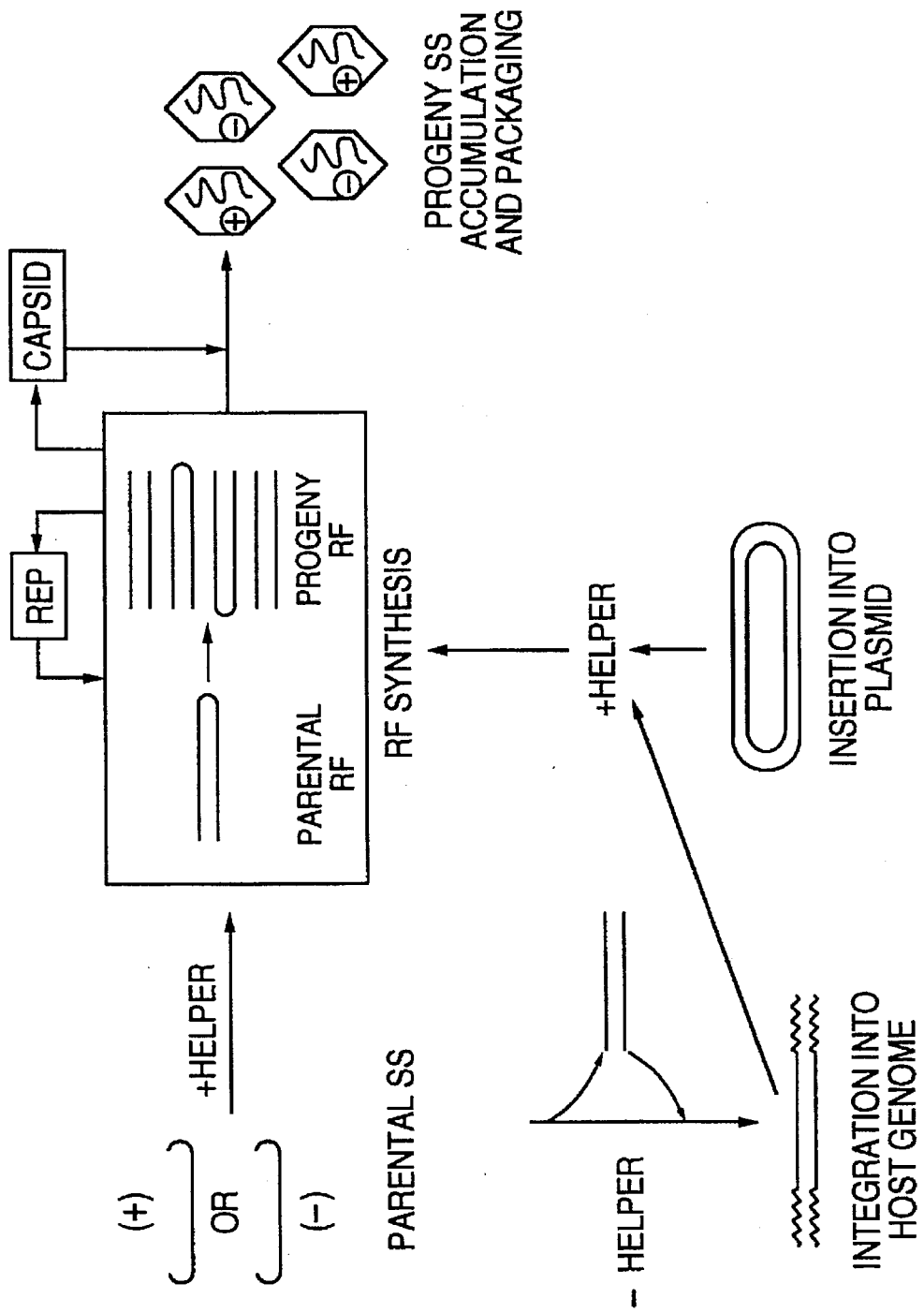
FIG. 1 is a diagram of the AAV life cycle.

AAV vectors have relevance for human gene therapy, particularly for diseases such as cystic fibrosis and sickle cell anemia. The invention described herein provides methods and materials for use in the production of high titers of recombinant AAV vectors for use in gene therapy.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, *Moleculal Cloning: A Laboratory Manual*, Second Edition (1989), *Oligonucleotide Synthesis* (M. J. Gait Ed., 1984), *Animal Cell Culture* (R. I. Freshhey, Ed., 1987), the series *Methods in Enzymology* (Academic Press, Inc.); *Gene Transfer Vectors for Mammalian Cells* (J. M. Miller and M. P. Calos eds. 1987), *Handbook of Experimental Immunology*, (D. M. Weir and C. C. Blackwell, Eds.), Current Protocols in Molecular Biology (F. M. Ausubel, R. Brent, R. E. Kingston, D. D. Moore, J. G. Siedman, J. A. Smith, and K. Struhl, eds., 1987), and Current Protocols in Immunology (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

The generation of high titers of recombinant AAV vectors comprised of heterologous polynucleotidee that require transcription is accomplished by the following method.

In the method cloned cells that contain a suitable AAV vector plasmid are provided. The AAV vector plasmid is comprised of the AAV ITR regions and a transcription promoter operably linked to a target polynucleotide. The transcription promoter that is linked to the target polynucleotide allows the formation of transcripts, and includes, for example, non-AAV promoters as well as AAV promoters such as $p_5$, $p_{19}$, $p_{40}$, and AAV ITR promoters. The transcription and/or translation products of the target polynucleotide are of use, preferably in gene therapy. Thus, target polynucleotides include genes to be delivered for gene therapy, for example, those encoding subunit chains of hemoglobin, enzymes, proteins such as the cystic fibrosis transmembrane conductance regulator (CFTR), and the like. Target polynucleotides may also be polynucleotides that when transcribed have activity as anti-sense molecules, as decoys that bind to transcription or translation factors, as ribozymes, and the like.

A requisite feature of the cloned cells provided for the method is that they contain at least one intact copy of the AAV vector plasmid that is stably integrated into the cell and that can be rescued by infection of the transfected cell with a helper virus such as adenovirus when complementary AAV rep or rep and cap functions are also provided.

In the examples shown infra we have used an AAVneo vector in which the initial selection of the cell line containing the vector was performed by geneticin selection. However, it would be obvious to one of skill in the art that to generate cell lines containing a vector, such as an AAV vector containing a CFTR gene, in which there is no selective marker included, it is straightforward to transfect the cells jointly with the desired vector plasmid and a second plasmid containing the selective marker. Following selection of cell clones on the basis of the selective marker, it would be obvious to use direct screening to readily identify those from which a vector can be rescued at high titer. One example of this is reported by Flotte et al. (1993a), although in that example the cells were rescued by infection with AAV virus and adenovirus. As recorded in Flotte et al. (1993a), producer cell lines containing a rescuable AAV vector that did not contain a selectable marker in the vector could also be obtained. In that example, the AAV vector plasmids comprised constructs containing the human CFTR cDNA operably linked to an AAV promoter comprised of the ITR. Cell lines containing stably integrated copies of these vectors were derived by co-transfection of the human epithelial cell line IB-3 with the AAV-CFTR vector plasmid and a second plasmid containing the selectable marker neo. After selection of colonies in geneticin, individual clones were obtained that contained the stably integrated vector from which the vector could be rescued by subsequent infection with helper adenovirus and wild-type AAV particles. This clearly enables the generation of clones having stably integrated copies of a vector in which the vector itself does not have a selectable marker.

The method also includes providing a complementing packaging plasmid from which Rep or Rep and Cap proteins can be expressed from rep or rep and cap genes. The packaging plasmid lacks overlapping homology with sequences in the vector between and including the AAV ITR sequences. Moreover, the combination of the packaging plasmid and vector cannot yield a complete AAV genome. In the example shown below, sequences of 120 nucleotides in length around the AAV $P_5$ promoter are absent from both the packaging plasmid and the vector. In addition, in the packaging plasmid the rep gene is not transcribed from the AAV $P_5$ promoter, but rather is operably linked to a heterologous transcription promoter that is not strongly autoregulated in a negative fashion by expression from rep.

In the preferred example of a packaging plasmid, such as shown by pRS5, we have used the HIV-LTR as the heterologous promoter but any heterologous promoter, and preferably a constitutive or inducible promoter may be used. The HIV-LTR is an example of both types of promoter. Generally, this promoter is inducible to a very high level of expression by the action of the tat protein. However, in the preferred example shown here, the HIV-LTR promoter shows high levels of constitutive expression of rep when used in 293 cells. This is because 293 cells express the adenovirus EIA gene product which is known to transactivate the HIV-LTR promoter. Thus, in 293 cells (which are preferred cell line for establishing vector containing cells) the additional transactivation of the HIV-LTR promoter in pRS5 may not be necessary to obtain a maximum level of functional rep expression. If vector-producing cells lines are made in other cells, then transactivation of pRS5, by addition of a tat expression plasmid such as pARtat (Antoni et al. 1991) may be desirable. Such cell lines might include any human cell lines such as HeLa, A549, KB, Detroit, WI38 or any cell lines in which appropriate helper functions can be expressed. When using human adenovirus as a helper, this might also include the monkey desired cell line, VERO. Alternatively, if herpesviruses or poxviruses such as vaccinia or avipox are used to provide helper function, then any appropriate human, rodent or simian cell line may suffice as the vector-producing cell.

The pRS5 packaging plasmid serves as a model of either an inducible or constitutive promoter. It would be obvious to anyone skilled in the art that many other inducible or constitutive promoter may be used in a packaging plasmid construct. The primary feature of the packaging plasmid is that it not contain the wild-type AAV $P_5$ promoter and therefore is not strongly negatively autoregulated by rep. Examples of other such promoters would be mutations of the wild-type $p_5$ promoter that remove homology with the parent wild-type promoter or that inactivate negative regulatory elements of this promoter such as the YYI region of the $p_5$ promoter. Examples of inducible promoters include: metal ion inducible promoters such as the metallothionein promoter; steroid hormone inducible promoters such as the MMTV promoter; or the growth hormone promoter; promoters which would be inducible by the helper virus such as adenovirus early gene promoter inducible by adenovirus E1A protein, or the adenovirus major late promoter; herpesvirus promoter inducible by herpesvirus proteins such as VP16 or 1CP4 or vaccinia or poxvirus inducible promoters or promoters inducible by a pox virus RNA polymerase or a bacterial promoter such as that from T7 phage which would be inducible by a pox virus RNA polymerase or a bacterial promoter such as that from T7 RNA polymerase.

There are many strong constitutive promoters that will be suitable for use as the heterologous promoter for rep expression in the packaging plasmid, including the adenovirus major later promoter, the cytomegalovirus immediate early promoter, the β action promoter, or the β globin promoter. Promoters activated by RNA polymerase III could also be used.

The efficacy of the packaging plasmid for complementation of the Rep and Cap functions for packaging the AAV vector plasmid can be tested using AAV expression vectors that lack the Rep and/or Cap function, and in addition contain a marker. Such expression vectors are known in the art, and include, for example, the pAAVp$_5$neo construct (Flotte et al., 1992). In the Examples the pAAVp$_5$neo was used as a vector construct for testing each of the packaging techniques described since it could be titered both for particle number by DNA dot-blot (Samulski, et al., 1989) and by neo-transducing titers.

The packaging plasmid is introduced into cells containing the integrated AAV vector plasmid by any suitable technique known in the art, including, for example, transfection, electroporation, and the like. After introduction of the packaging plasmid, the cells are grown for 3 to 5 days under conditions that allow replication of AAV, lysates are prepared, and the recombinant AAV vector particles are purified by techniques known in the art.

The examples presented below are provided as a further guide to the practitioner of ordinary skill in the art, and are not to be construed as limiting the invention in any way.

The plasmid pRS5 in the *E. coli* DH5 cell line (*E. coli*::pRS5 strain) was deposited on Nov. 9, 1993 with the American Type Culture Collection (ATCC), 12301 Parklawn Dr., Rockville, Md. 20852, and has been assigned the Accession Number 69483. The deposit was made under the terms of the Budapest Treaty. Upon allowance and issuance of this application as a United States Patent, all restriction on availability of the deposit will be irrevocably removed; and access to the designated deposits will be available during pendency of the above-named application to one determined by the Commissioner to be entitled thereto under 37 CFR § 1.14 and 35 USC § 1.22. Moreover, the designated deposits will be maintained for a period of thirty (30) years from the date of deposit, or for five (5) years after the last request for the deposit; or for the enforceable life of the U.S. patent, whichever is longer. The deposited materials mentioned herein are intended for convenience only, and are not required to practice the present invention in view of the descriptions herein, and in addition these materials are incorporated herein by reference.

EXAMPLES

Example 1

Packaging plasmid pRS5

In packaging plasmid pRS5 the AAV $p_5$ promoter is replaced by a heterologous promoter so that expression of the rep gene polypeptide does not negatively autoregulate its own synthesis.

Figure 2:
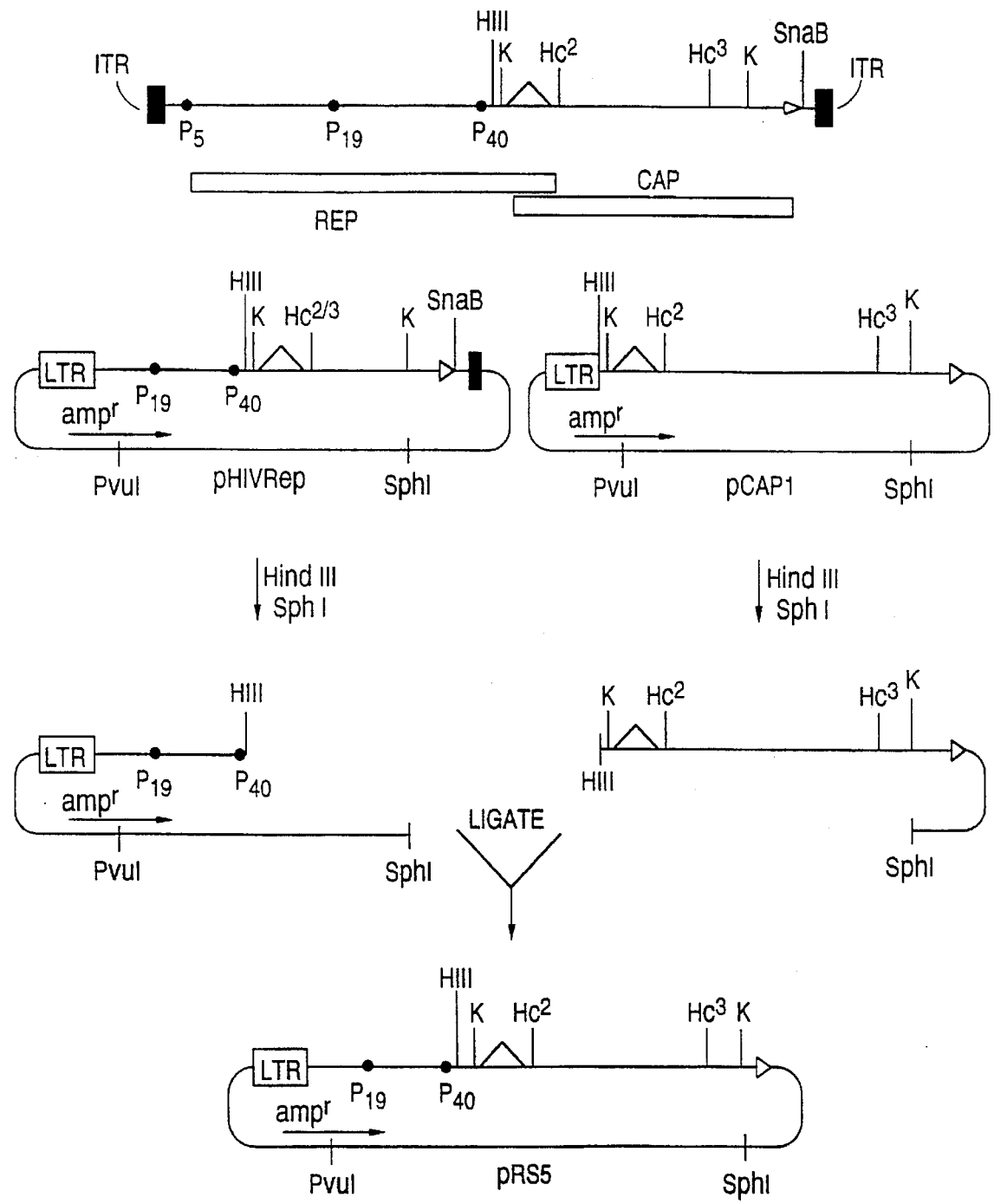
FIG. 2 is a scheme showing the production of the packaging plasmid pRS5, and the relationship of the HIV1-LTR promoter and the coding sequence of AAV2 rep and cap genes.

The plasmid pRS5 was constructed by ligating the large (5 kb) HindIII to SphI fragment of the previously-described pHIVrep (Antoni et al., *J. Virol.*, 65:396–404) plasmid (containing the HIV-LTR promoter and rep-gene sequences including AAV nucleotides 263 to 1886 flanked by pBR322 plasmid sequence) with the HindIII to SphI fragment from a plasmid called pcap1 (containing the AAV cap gene from nucleotides 1886 to 4491 without the AAV-ITR again flanked by pBR322 sequences) (see FIG. 2). After ligation of these two fragments a packaging plasmid, pRS5, was produced in which the AAV-rep gene (Rep 68 and 78 proteins) is transcribed from the HIV-LTR promoter with the internal AAV $p_{19}$ and $p_{40}$ promoters transcribing the smaller Rep products (40 kD and 52 kD Rep proteins) and the capsid proteins, respectively. Thus pRS5 contains the entire AAV coding sequence within the AAV nucleotide sequence from nucleotide 263 to 4491 which includes the rep coding sequence for Rep 78 and Rep 68 operably linked to the heterologous HIV-LTR promoter and expresses Rep 52 and Rep 40 from the AAV $p_{19}$ promoter and the AAV capsid proteins from the $p_{40}$ promoter. The map of this construct is shown in FIG. 1.

The pAAVp$_5$neo construct (Flotte et al., 1992) was used as a vector construct for testing each of the packaging techniques described since it could be titered both for particle number by DNA dot-blot (Samulski, et al., 1989) and by neo-transducing titers.

Example 2

Cell Lines

Human 293–31 cells (Graham et al., 1967, *J. Gen. Virol.*, 36:59–72). were grown in Eagle's Modified Essential Medium with 10% fetal calf serum at 37° C. in 5% $CO_2$. The 293 cell line was used for both packaging of vector preparations and for neo transduction experiments to verify the neo-transducing titers.

Example 3

Packaging of AAV virions with an HIV-LTR promoter-rep gene plasmid

The pRS5 construct was used to package the pAAVp$_5$neo vector plasmid by co-transfection into adenovirus type 5 (Ad5)-infected 293 cells (Flotte et al., 1992). A total of ten 10-cm dishes each containing $2 \times 10^6$ 293 cells (semiconfluent) were infected with $2 \times 10^6$ p.f.u. of Ad5 (m.o.i.=1) 1 hr prior to transfection with 12.5 µg each of pRS5 and pAAVp$_5$neo. Cells were then incubated for 3 days at 37° C. prior to harvesting. Cells were then scraped and pooled by low-speed centrifugation (4000 rpm×10 min).

The cell pellet was then resuspended in 4 ml of 10 mM Tris-HCl, pH 8.0, lysed by threefold freeze-thaw, pushed through a 25 g needle several times to decrease viscosity, and treated with micrococcal nuclease (40 µl of 300 µ/µl stock, incubated at 37° C.×20 min., and then at 4° C. for 10 min. CsCl was then added to a final density of 1.41 g/cc. Each tube was overlaid with 0.5 to 1.0 ml mineral oil and centrifuged in a swinging bucket rotor (SW50) at 35,000 rpm at 4° C. for 12 hr.

Serial 0.5 ml fractions were then collected and each was titered by DNA dot-blot hybridization (Samulski et al., 1989), with 10-fold dilutions of each fraction blotted onto nitrocellulose filters and hybridized with a $^{32}$P-labeled DNA probe prepared from a 2.3 kb neo gene fragment using the Boehringer Mannheim random-priming kit. The selected fractions were then dialyzed against Ringer's balanced salt solution, pH 7.4, and saved at −20° C. for use in transducing titer experiments.

Example 4

Determination of transducing titers of AAV-neo vector stocks

AAV-neo vector stocks produced as outlined above were titered in 293-31 cells by infecting 293-31 cells at 10-fold increasing particle multiplicities ranging from 10 to 1000 particles per cell. In each case cells were seeded into microtiter wells at $10^4$ cells per well, and then infected for 2 hr by direct inoculation of vector into the medium. The cells from each well were then trypsinized 24 hr later and plated onto 4–100 mm dishes. Three dishes of each set were then selected in G418 at a dose of 200 µg/ml (active, beginning at 48 hr after the original infection). The fourth dish of each set was grown without G418 as a control for plating efficiency. Cells were selected for 10 to 14 days, and then stained with Safranin Red. Geneticin-resistant colonies were counted and a transduction frequency was determined by dividing the mean number of gene colonies in each set by the number of colonies seen in the plating efficiency control plate. A transducing unit (t.u.) in this assay was then defined as that volume of inoculum per cell required to transduce 63% of cells to geneticin resistance.

Example 5

Improvement of co-transfection AAV-vector packaging by using an HIV-LTR promoter expression vector In Table 1 (experiments 1 to 3) are shown the results of DNA dot-blot titrations of AAV-neo particle preparations produced by the previously established pAAV/Ad co-transfection technique and a parallel pRS5 co-transfection.

TABLE 1

Particle Titer of AAV Vector Preparations

| Expt # | Cells | Vector Production Method[a] DNA Transfected | | Vector Particle Titer[b] Titer (particles/ml) |
|---|---|---|---|---|
| | | Vector Plasmid | Packaging Plasmid | |
| 1 | 293 | pSA206 | pAAV/Ad | $4.0 \times 10^9$ |
| 2 | 293 | pSA206 | pRS5 | $3.0 \times 10^{10}$ |
| 3 | 293 | pSA206 | pRS5 + pARtat | $4.0 \times 10^{10}$ |
| 4 | neo4-6 | — | RS5 | $2.6 \times 10^{11}$ |

[a]The vector preparations were derived as follows. All the vector preparations represent the AAVneo vector derived from the vector plasmid pAAVp5neo (pSA206). In experiments 1, 2, and 3 the vector preparation was derived by infection of 293 cells with adenovirus as helper and co-infection of the infected cells with the vector plasmid pAAVp5neo (pSA206) and the packaging plasmid which was either pAAV/Ad, pRS5 or pRS5 plus pARtat as indicated. In experiment 4 the vector was obtained by rescue of an integrated vector from the cell line neo4-6 by transfection of the cell line with the packaging plasmid pRS5 in the presence of an infecting adenovirus5 as the helper. The cell line neo4-6 was derived by transfection of 293 cells with the vector plasmid pAAVp5neo (pSA206) and selection with the antibiotic G418 (geneticin) for geneticin resistance. All the vector preparations were purified by banding in CsCl.
[b]The purified vector preparations were assayed to determine the particle titer by dot-blot assay.

The results in Table 1 show that titers achieved with the pRS5 construct introduced by co-transfection (experiment 4) were approximately five to ten-fold higher than those obtained using the pAAV/Ad packaging plasmid. The addition of the HIV trans-activator of transcription (tat) gene by plasmid tri-transfection resulted in very little additional packaging efficiency. In the experiment displayed in FIG. 3, there was only a 30% increase in the particle titer of the maximal-titer fraction, from $3.0 \times 10^{10}$ with pRS5 alone to $4.0 \times 10^{10}$ with pRS5+pARtat. Based on these results, it seemed likely that the levels of rep and cap expression were no longer limiting in this technique.

Figure 3:
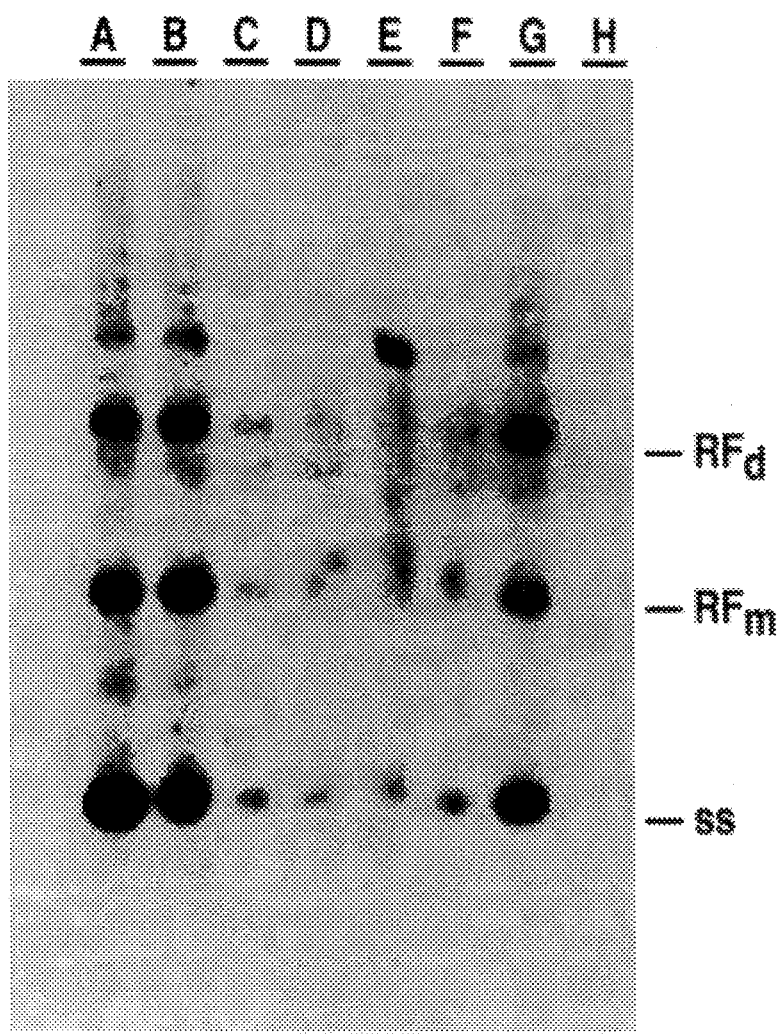
FIG. 3 is a half-tone reproduction of Southern blots of Hirt extraction DNA samples that shows rescuable intact AAV-neo genomes present in stable cell lines.

The experiment in FIG. 3 was performed as follows.

Example 6

Rescue of intact AAV-neo genomes present in stable cell lines

In this example, a culture of $2 \times 10^6$ human 293 cells was transfected with 5 micrograms of the AAV vector plasmid pAAVp5neo (pSA206). Individual colonies were selected for geneticin resistance using 200 micrograms of active G418 (Gibco-BRL) per ml of medium, beginning 48 hr after transfection. Individual G-418-resistant colonies were isolated with sterile cloning cylinders and expanded into stable cell lines. From several of these cell lines, $2 \times 10^6$ cells were infected with both adenovirus type 5 (moi=2) and wild type AAV2 (moi=2). Forty-eight hr later, low molecular weight DNA was selected using the Hirt high salt-detergent procedure and analyzed by 0.7% agarose gel electrophoresis and Southern blotting with a random-primed $^{32}$P-labelled neo DNA probe. The results of the Southern blot hybridization of Hirt-extracted DNA is shown in FIG. 3.

The Figure shows that from 7 to 8 individual cell lines examined (tracks A through G), the vector sequence could be rescued and replicated. Track H shows an example of one geneticin-resistant cell line from which the vector could not be rescued.

The expected intracellular replicating species of the vector genomes (RFm for monomer duplex replicating form and RFd for duplex dimer replicating form) and the progeny single-strand genomes (SS) are indicated. In at least 6 of the 8 examples (tracks A through D and Tracks F and G) unrearranged copies of the vector were rescued.

Example 7

The use of cell lines with integrated rescuable AAV vector improves packaging efficiency After improving the expression of AAV-rep and cap genes with the pRS5 construct, we sought to further improve the efficiency of packaging by producing uniform cell populations containing integrated but rescuable copies of the AAV-neo vector genome. The combination of pRS5 transfection of rep and cap with the stable addition of the pAAVp5neo vector to the cell lines resulted in a significant improvement in packaging efficiency.

Cell lines produced by transfecting AAV-p5neo by infecting with both wild-type AAV2 and Ad5 at an m.o.i. of 5 for each virus. Hirt extraction was used to isolate replicating viral DNA, and these DNA samples were analyzed to electrophoresis and Southern blot hybridization using a $^{32}$P-labeled neo probe. As shown in FIG. 3, rescuable AAV-neo recombinants were present in nearly all of these cell lines. The pattern of bands, as expected, included single strands (fuzzy band near bottom of gel), duplex monomer of 2.7 kb size, dimer of 5.4 kb, larger multimeric forms.

Two cell lines made in a similar fashion and designated neo4-6 and neo4-9 were constructed and used for subsequent packaging experiments. A direct comparison was made between co-transfection of pRS5 and pAAVp$_5$neo into 293 cells and single transfection of pRS5 into either the neo4-6 or neo4-9 cell lines. As shown in Table 1, the neo4-6 cell line produced titers of packaged AAV-neo that were $2.6 \times 10^{11}$. This particle titer represented a severalfold improvement over the 293 cell co-transfection method, and yielded the highest titers of any method or combination of methods used. The total particle titer of near $2.6 \times 10^{11}$ particles was achieve beginning with $2 \times 10^7$ cells and so represents a yield of $10^4$ particles per cell.

Figure 4:
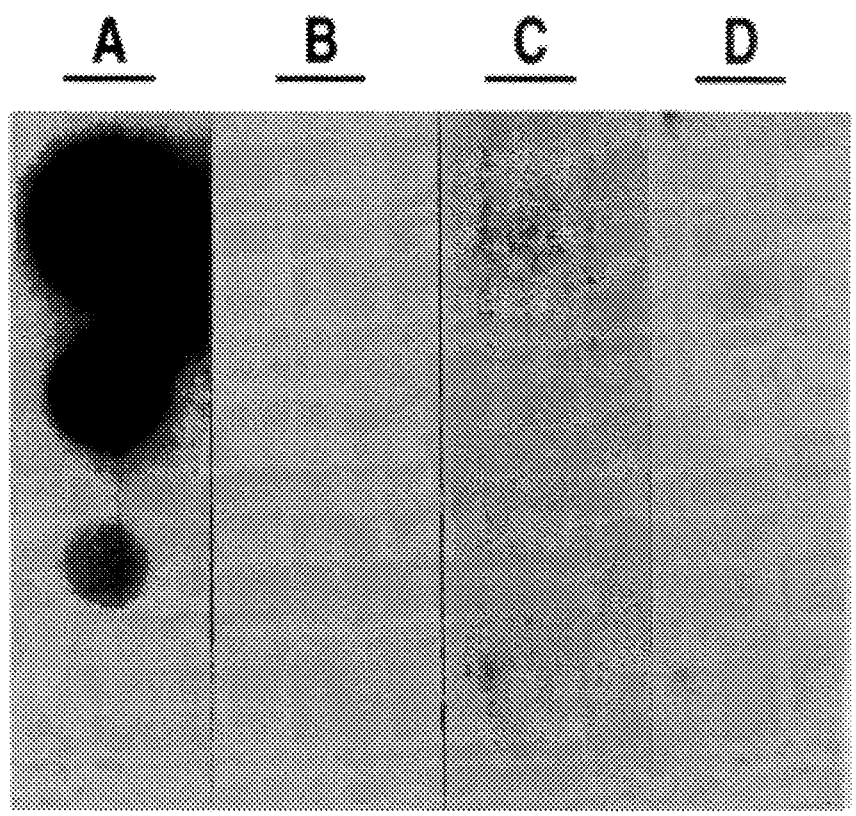
FIG. 4 is a half-tone reproduction of dot-blot hybridizations comparing the detection of neo in control and packaged AAV-neo genomes.
Figure 5:
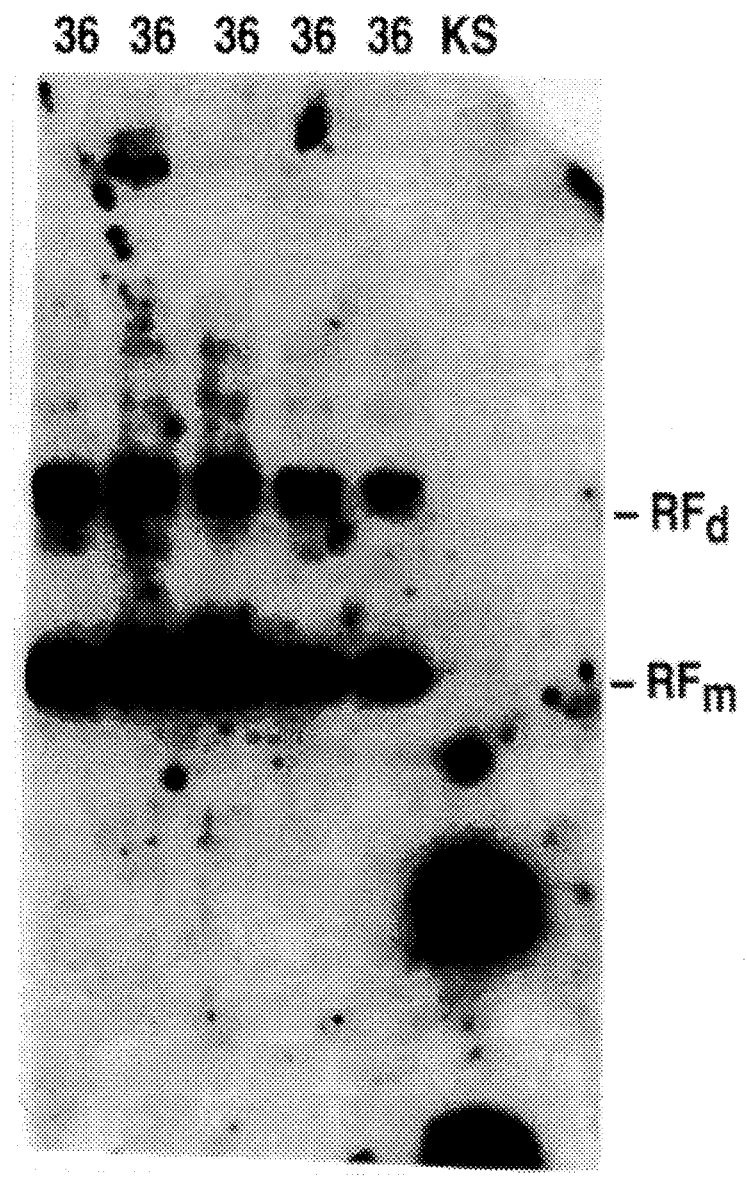
FIG. 5 is a half-tone reproduction of Southern blots of Hirt extraction DNA samples that shows rescue of the AAV CFTR vector (TRF42) from 293 cell vector producing clones.

The assays above are all based on a DNA/dot-blot technique which could theoretically also detect copies of AAV-neo genomes which had not been packaged into AAV particles. The results of two types of control experiments excluded that possibility. First, AAVp$_5$neo and pRS5 plasmids were co-transfected into 293 cells as previously, but in the absence of Ad5 infection. Lysates of these cells were treated as with any of the other preparations mentioned above. As shown in FIG. 4, control dot-blot hybridizations indicated that the neo signals reflected packaged AAV-neo genomes.

The DNA dot-blot hybridization was performed as follows: Beginning with 50 microliters Of each fraction, five 10-fold serial dilutions were performed in PBS. To lyse the virions, 1/10 volume (5 µl) of 3N NaOH was added, and the mixture was incubated at 65° C. for 1 hr. An equal volume (50 µl) of 2M NH$_4$OAc, pH 7.0, was added, and the total 100 µl volume was transferred onto 0.45 µm nylon filters with a Schleicher and Schuell Minifold I microsample filtration manifold. These filters were then hybridized with random-primed $^{32}$P-labelled neo DNA probes under standard conditions.

Serial 10-fold dilutions of control stocks prepared as described were compared with dilutions of an AAV-neo stock prepared by pRS5 transfection of the neo4-9 cell line after adenovirus infection (shown in column A). Column B shows pRS5 transfection of the neo4-9 cell line without adenovirus infection. Column C shows adenovirus infection of neo 4-6 cell line without pRS5 transfection. Column D shows adenovirus infection of pSA206-transfected 293 cells without pRS5 co-transfection. In no case did the carried-over cell or plasmid DNA give a significant neo signal. The results in FIG. 4 show that no detectable AAV-neo signal was present in the DNA/dot-blot hybridization from that experiment, indicating clearly that plasmid DNA was not present in these purified preparations.

A direct comparison was then performed of the transducing titer of the AAV-neo vector stocks produced in the dual plasmid transfection system or by the rescue of vector from stable lines. As indicated in Table 2, the transduction frequency obtained with an equivalent number of vector particles produced in either system was similar. This indicates that the vector particles generated by rescue of the vector from stable cell lines were of equal biological efficiency and transducing potential as those produced in the dual transfection. Thus, the vectors rescued from cell lines did not have any significant biological alterations.

TABLE 2

Biological Equivalence of AAV-neo Vector Preparations.[a]

| Vector Preparation[b] | Particle Multiplicity[c] | Percent Transduced[d] |
|---|---|---|
| neo4-6 | 10 particles/cell | 23.1% |
| neo4-9 | 10 particles/cell | 44.4% |
| pRS5 trf | 10 particles/cell | 32.9% |
| pRS5 + tat | 10 particles/cell | 23.7% |

[a]The transduction efficiency of several AAV-neo vector preparations was compared in the 293 cell line.
[b]The vector preparations were derived as follows: All the vector preparations represent the AAVp$_5$neo vector derived from the vector plasmid pAAVp$_5$neo. The preparations designated neo4-6 and neo4-9 were obtained by rescue of an integrated vector from the cell lines 4-6 or 4-9 by transfection of the cell line with the packaging plasmid pRS5 in the presence of an infecting adenovirus5 as the helper. The cell lines 4-6 and 4-9 were derived by transfection of 293 cells with the vector plasmid pAAVp$_5$neo and selection with the antibiotic G418 (geneticin) for geneticin resistance. The vector preparation designated pRS5 trf was derived by direct co-transfection of 293 cells with the vector plasmid pAAVp$_5$neo and the packaging plasmid pRS5 in the presence of an infecting adenovirus5 as the helper. The vector preparation pRS + tat was also obtained by direct transfection exactly as for pRS5 trf except that the co-transfection also included the plasmid pARtat, which expresses the HIV tat transcriptional activator.
[c]Cultures of $10^4$ 293 cells were infected with $10^5$ particles of AAV-neo vector preparations. Thus, each vector preparation was used to infect the 293 cells at a multiplicity of 10 vector particle per cell.
[d]The infected cultures were then grown under conditions to select geneticin-resistant colonies. The percent of 293 cells stably transduced to geneticin resistance (i.e., the transduction frequency) was claculated as the number of geneticin-resistant colonies from the individual culture divided by the number of colonies obtained in a control culture not treated with geneticin.

The above results indicate that the combined modifications described here can yield increases in vector titers of approximately 50- to 100-fold. Also, as compared with the previously published reports (e.g., Samulski et al., this procedure can give vector particle titers of at least $2 \times 10^{11}$, which is three orders of magnitude higher than that previously attained from a similar number of cells (i.e., human 293 cells grown in a total of ten 10-cm cell culture dishes).

Example 8

Packaging of AAV Vectors encoding CFTR

An AAV-CFTR vector, pTRF42, containing the CFTR cDNA expressed from an AAV ITR as the promoter in the absence of a selectable marker was used to generate stable vector producer lines in the 293 cell line by co-transfection with a pSVneo plasmid. This vector was rescuable from the stable cell lines, and the rescued vector was intact and unrearranged.

The construction of pTRF42 has been described (Flotte et al. 1993a, *J. Biol. Chem.* 268:3781–3790). This construct contains an AAV-CFTR vector consisting of 145 nucleotides of the AAV 5' end (the ITR) followed by an in-frame ATG (Met) initiation codon, reading directly into the CFTR coding sequence from amino acid 119. The remainder of the CFTR cDNA is intact down through the native termination codon and up to nucleotide 4629 of the original sequence. This is followed by a synthetic polyadenylation signal, and then by AAV nucleotides 4490–4681 (3' ITR). Four micrograms of this vector was co-transfected with one microgram of the pSV2neo plasmid, into $2 \times 10^6$ human 293 cells, which were then selected with 200 µg of active G-418 beginning 48 hr after transfection. G-418-resistant clones were then isolated with cloning cylinders and expanded. Clones were analyzed by rescue with combined wild-type AAV2 and Ad5 infection (moi=2 for each) as had been done for the neo-vector containing lines. The low molecular weight DNA (Hirt) extracts were again analyzed by 0.7% agarose gel electrophoresis and Southern blotting with a random-primed $^{32}$P-labelled CFTR cDNA probe. Once again, the cell lines were found to have rescuable, intact vector sequences of the sizes predicted for monomer and dimer replicating forms (RF), namely 4.6 and 9.2 kb, respectively. This confirmed the utility of the approach utilizing rescuable vector-containing cell lines with the clinically significant example of an AAV-CFTR vector.

The principles and teachings described above have been applied to produce additional illustrations of the present invention, some of which are described below, that further demonstrate the usefulness of the present invention.

Example 9

Integration of the lacZ gene into Lung Airway Epithelium

The in vivo activity of vectors packaged by the preceding methods was tested using the lacZ gene which encodes an enzyme with β-galactosidase activity. The AAVp$_5$lacZ vector was made by digesting the pAAVp$_5$neo construct with HindIII and BamHI and ligating the large fragment (containing the AAV ITRs flanking the AAVp$_5$ promoter and a synthetic polyadenylation sequence) with a HindIII to BamHI fragment from pSVBgal containing the E. coli lacZ gene. This initial construct was then modified by digestion with HindIII and KpnI, blunting with T4 polymerase (Boehringer Mannheim), and religation of the large fragment. This final manipulation allowed for the removal of an intervening segment of sequence containing four ATG codons out of frame with the lacZ coding sequence. The vector was then packaged using the pRS5 plasmid as described above.

Aliquots of packaged AAVp$_5$lacZ containing $10^{10}$ particles in 0.2 to 0.5 ml were administered by intraperitoneal injection into three weaning C57BL mice. Aliquots of the same vehicle solution against which the vector had been dialyzed were injected into three additional mice which served as controls. The weight of these mice was approximately 30 gm each, with an estimated total body cell number of between $10^8$ and $10^9$ cells. The average vector dose per cell was, therefore, between 10 and 100 particles per cell, depending on blood flow. Animals were sacrificed four days later by pentobarbital overdose, and samples of abdominal wall, lungs, liver, spleen, kidneys, and pancreas were harvested and fixed in 2.5% glutaraldehyde.

An in situ PCR assay was performed on 5-micron parafin embedded tissue sections, using vector-specific primers and a non-radioactive digoxigenin-dUTP, anti-digoxigenin, alkaline phosphatase immunodetection system as previously described (Flotte et al., 1993). Primers were selected from within the lacz sequence (5'-primer: 5'-ACAACTTTAACGCCGTGCGCT-3'; 3'-primer: 5'TGCAGGAGCTCGTTATCGCTA-3'). After a hot-start at 82° C., a 40-cycle PCR was performed with direct incorporation of digoxigenin-labeled dUTP (Boehringer Mannheim) in the reaction products. Digoxigenin-labeled nucleotides were then detected with an alkaline phosphatase-tagged anti-digoxigenin antibody (Genius III kit, Boehringer Mannheim), and an immunohistochemical stain (NBT, X-phos).

Various tissue sections for vector- and control-injected mice were examined by light microscopy. The cells containing vector DNA were indicated by a dark purple-brown reaction product overlying the nucleus. Staining was clearly observed in sections from vector-injected mice, but not in those from controls. Vector DNA was detected in all cell types within the lungs, as well as in most hepatocytes and pancreatic acinar cells. After absorption via the lymphatics, vector particles would have entered the venous circulation and encountered the pulmonary circulation, which likely accounts for the very efficient gene transfer in the lung. After passing through the pulmonary into the systemic circulation, vector particles would likely have been distributed most effectively to other organs with high blood flow.

Example 10

Expression of the lacZ gene In Vivo

Serial sections of the same tissue samples used for the in situ PCR detection were stained for β-galactosidase activity with X-gal reagent (0.2%, 37° C., 16 hr). Sections from mice injected with AAVp$_5$lacZ were compared with those injected with vehicle controls. No endogenous β-galactosidase activity was detectable in control animals in sections taken from lung, spleen, liver, pancreas, kidney, or peritoneum.

Sections of lung showed lacZ expression in entire segments of airway epithelium of vector-injected animals but not controls. In some of the airways, >75% of 200 cells examined were positively stained. Approximately 25% of airways demonstrated this degree of positive staining (4 to 6 airways examined per sections, one to two sections per animal), while other regions of the lung had lower levels of expression.

Spleen sections demonstrated β-galactosidase activity in non-lymphoid areas of vector-injected animals, but not controls. Lymphoid follicles within the spleen were essentially negative. Infrequent staining was seen in non-epithelial cells within the lungs or in cells of the liver, abdominal wall, and kidneys of vector-treated animals, while no expression was detectable in the pancreas.

The distribution of vector DNA, as detected by an in situ PCR assay, is compared with the distribution of β-galactosidase activity in Table 3, as follows (n=3): (—) no staining, (+) X-gal stained cells. <1%, (++) 1–25% staining, (+++)>25% staining, (nd) not done.

TABLE 3

| Tissue Distribution of lacZ Gene Transfer and Expression | | |
|---|---|---|
| Organ (Tissue) | in situ PCR | X-gal staining |
| Lung (Airway) | +++ | +++ |
| Lung (Alveoli, vessels) | +++ | + |
| Spleen (Non-lymphoid) | +++ | +++ |
| Spleen (Lymphoid follicles) | + | — |
| Liver | +++ | + |
| Pancreas | +++ | — |
| Kidney | nd | ++ |
| Peritoneum | nd | — |

Expression of β-galactosidase activity therefore depends both on the distribution of the DNA vector, and the tissue specificity of the promoter. For example, the P$_5$ promoter is very active in airway epithelial cells, but much less active in other cells that have been tested, such as those derived from the pancreas.

Example 11

Integration and expression of the CD44 gene in lung carcinoma cells

The pSAcd44 vector, which expresses the cell-surface marker CD44 from the P$_5$ promoter, was subcloned directly from the pSA206 (AAVp5neo) construct. Particle numbers were determined by dot-blot analysis. This vector and the pRS5 packaging plasmid were co-transfected the lung carcinoma cell lines H209 and H82. Various doses of the vector were tested in $4 \times 10^4$ cells per aliquot. Forty eight to 72 hours after transfection, the cells were fluorescently stained for cell-surface gene expression using an anti-CD44 antibody. The cells were then passed through a fluorescence-activated cell counter to determine the proportion that were positively stained.

Figure 6A:
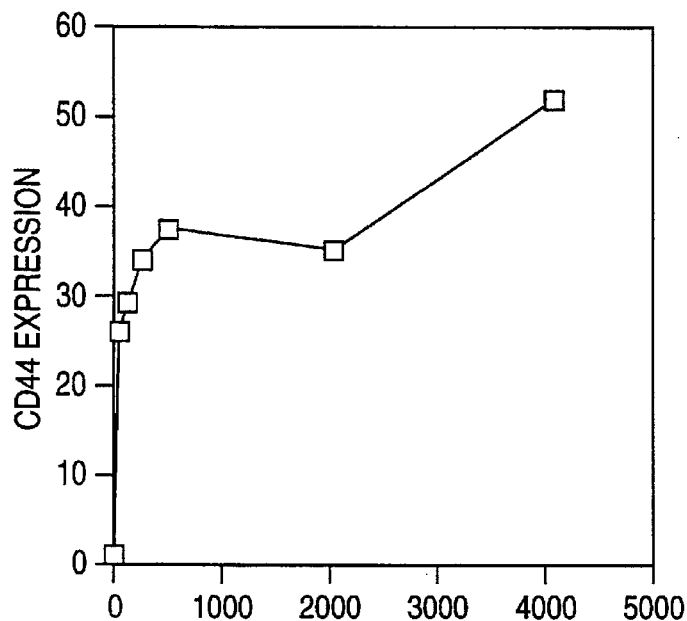
FIG. 6 is a graph of the percentage of lung carcinoma cells stained for the CD44 marker, as determined by antibody staining and FACS analysis.
Figure 6B:
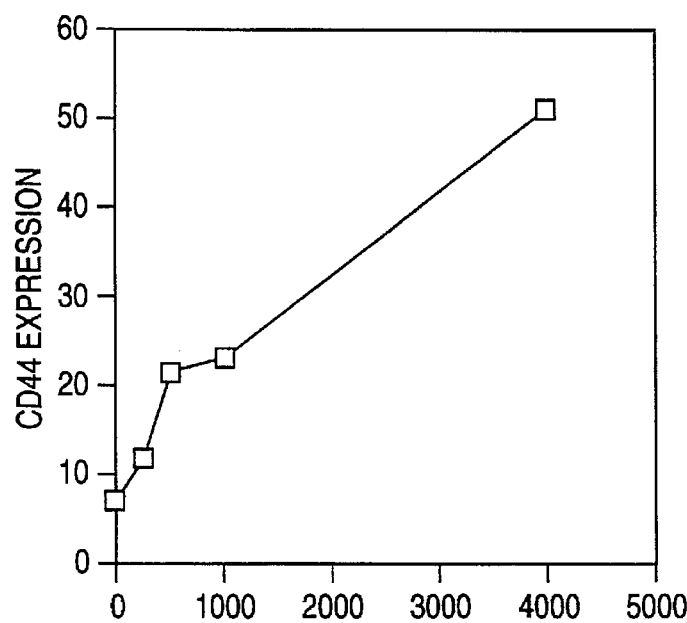

Results of this analysis are shown in FIG. 6. Virus titers are expressed in units of $10^4$; thus, "1000" on the horizontal axis represents 250 vector particles per carcinoma cell. High frequency of CD44 expression was accomplished at doses as low as 100 particles per cell.

We claim:

1. A process for the generation of high titers of AAV recombinant vectors comprising:
   (a) providing cells containing at least one intact copy of a stably integrated recombinant AAV vector, wherein the AAV vector comprises AAV inverted terminal repeat (ITR) regions and a transcription promoter operably linked to a target polynucleotide, and wherein the expression of the rep gene is limiting in said cells;
   (b) providing an AAV packaging plasmid that allows expression of the product of the rep gene, wherein in the plasmid the rep gene is operably linked to a heterologous promoter, and wherein the packaging plasmid lacks overlapping homology with AAV sequences in the vector in the cell provided in (a);
   (c) inserting the AAV packaging plasmid into the cell provided in and incubating the cell under conditions that allow replication and packaging of AAV; and
   (d) isolating recombinant AAV vectors produced in step (c).

2. The process of claim 1 wherein the heterologous promoter of step (b) is HIV-LTR.

3. The process of claim 1 wherein the packaging plasmid is pRS5.

4. The process of claim 1 wherein the target polynucleotide encodes a cystic fibrosis transmembrane conductance regulator (CFTR) polypeptide.

5. The process of claim 2 wherein the target polynucleotide encodes a cystic fibrosis transmembrane conductance regulator (CFTR) polypeptide.

6. The process of claim 3 wherein the target polynucleotide encodes a cystic fibrosis transmembrane conductance regulator (CFTR) polypeptide.

7. A packaging system for the generation of high titers of AAV recombinant vectors comprising:
   (a) cells containing at least one intact copy of a stably integrated recombinant AAV vector, wherein the AAV vector comprises AAV inverted terminal repeat (ITR) regions and a transcription promoter operably linked to a target polynucleotide, and wherein the expression of the rep gene is limiting in said cells; and
   (b) an AAV packaging plasmid that allows expression of the product of the rep gene, wherein in the plasmid the rep gene is operably linked to a heterologous promoter, and wherein the packaging plasmid lacks overlapping homology with AAV sequences in the vector in the cell provided in (a).

8. The packaging system of claim 7 wherein the heterologous promoter in step (b) is HIV-LTR.

9. The packaging system of claim 7 wherein the packaging plasmid is pRS5.

10. The packaging system of claim 7 wherein the target polynucleotide encodes a cystic fibrosis transmembrane conductance regulator (CFTR) polypeptide.

11. The packaging system of claim 8 wherein the target polynucleotide encodes a cystic fibrosis transmembrane conductance regulator (CFTR) polypeptide.

12. The packaging system of claim 9 wherein the target polynucleotide encodes a cystic fibrosis transmembrane conductance regulator (CFTR) polypeptide.

13. A packaging plasmid for the production of high titers of AAV recombinant vectors wherein said packaging plasmid allows expression of the product of the rep gene, and further wherein the plasmid comprises the rep gene operably linked to a heterologous promoter.

14. The packaging plasmid of claim 13 wherein the promoter in the packaging plasmid to which rep is operably linked is HIV-LTR.

15. A packaging plasmid according to claim 13, wherein the plasmid is pRS5.

* * * * *

UNITED STATES PATENT AND TRADEMARK OFFICE
CERTIFICATE OF CORRECTION

PATENT NO. : 5,658,776

DATED : August 19, 1997

INVENTOR(S) : Terence R. Flotte, Barrie J. Carter, William B. Guggino, Rikki Solow It is certified that errors appear in the above-identified patent and that said Letters Patent is hereby corrected as shown below:

(1) Under Attorney, Agent, or Firm, line 1 should read "Morrison & Foerster L.L.P."

(2) Claim 1, part (c), line 2 should read "provided in (a) and..."

Signed and Sealed this

Thirtieth Day of December, 1997

Attest:

BRUCE LEHMAN

*Attesting Officer*    *Commissioner of Patents and Trademarks*